United States Patent
McCaffrey et al.

(10) Patent No.: US 6,927,851 B2
(45) Date of Patent: Aug. 9, 2005

(54) METHODS AND APPARATUS TO IMPROVE THE SENSITIVITY AND REPRODUCIBILITY OF BIOLUMINESCENT ANALYTICAL METHODS

(75) Inventors: John T. McCaffrey, Cheshire, CT (US); Szilveszter Jando, Waterbury, CT (US); Sunita Carrasko, Danbury, CT (US)

(73) Assignee: Neogen Corporation, Lansing, MI (US)

( * ) Notice: Subject to any disclaimer, the term of this patent is extended or adjusted under 35 U.S.C. 154(b) by 340 days.

(21) Appl. No.: 09/821,571

(22) Filed: Mar. 29, 2001

(65) Prior Publication Data

US 2001/0038450 A1 Nov. 8, 2001

Related U.S. Application Data

(60) Provisional application No. 60/193,974, filed on Mar. 31, 2000.

(51) Int. Cl.$^7$ ............................. G01J 3/30; G01N 21/76
(52) U.S. Cl. ......................... 356/311; 422/52; 436/172
(58) Field of Search .................. 356/39, 311; 436/164, 436/165, 172; 422/52, 82.05

(56) References Cited

U.S. PATENT DOCUMENTS

| | | | |
|---|---|---|---|
| 3,849,653 A | 11/1974 | Sakaide et al. ............. 250/361 |
| 3,933,592 A | 1/1976 | Clendenning ............ 195/103.5 |
| 4,014,745 A | 3/1977 | Fletcher et al. ...... 195/103.5 K |
| 4,098,728 A | 7/1978 | Rosenblatt | |
| 4,144,134 A | 3/1979 | Plakas ................. 195/103.5 M |
| 4,246,340 A | 1/1981 | Lundin et al. .................. 435/8 |
| 4,353,868 A | 10/1982 | Joslin et al. ................ 422/101 |
| 4,608,344 A | * | 8/1986 | Carter et al. .................. 436/34 |
| 4,672,039 A | | 6/1987 | Lundblom .................. 435/291 |
| 4,689,305 A | | 8/1987 | Stiffey et al. ............... 435/291 |

(Continued)

FOREIGN PATENT DOCUMENTS

| | | | | |
|---|---|---|---|---|
| EP | 0 038 134 B1 | 3/1981 | | |
| EP | 0 309 429 A2 | 9/1988 | | |
| EP | 0 439 525 B1 | 10/1989 | | |
| EP | 0 717 840 B1 | 8/1994 | | |
| GB | 2218803 A | 11/1989 | | |
| GB | 2281966 A | * 3/1995 | .......... G01N/21/01 |
| WO | WO 90/04775 | 5/1990 | | |
| WO | WO 95/07457 | 3/1995 | | |
| WO | WO 95/25948 | 9/1995 | | |
| WO | WO 97/23596 | 7/1997 | | |
| WO | WO 98/27196 | 6/1998 | | |
| WO | WO 98/49544 | 11/1998 | | |
| WO | WO 200070011 A1 | * 11/2000 | ............. B01L/3/00 |

OTHER PUBLICATIONS

Colaco, Camilo et al; Extraordinary Stability of Enzymes Dried In Trehalose: Simplified Molecular Biology; Bio/Technology vol. 10; Sep. 1992; pp. 1007–1011.

(Continued)

*Primary Examiner*—Zandra V. Smith
*Assistant Examiner*—Gordon J. Stock, Jr.
(74) *Attorney, Agent, or Firm*—Ian C. McLeod

(57) ABSTRACT

A hand-held assay device measuring chemiluminescence generated by as ample of ATP or other entity capable of chemically reacting to generate photoluminescence includes a photodiode detecting light which is emitted from the sample to produce a sample signal, another photodiode generating a reference signal in response to environmental changes, switched integrators amplifying the sensor signal over a controllable integration time to detect an output signal indicative of the presence of the sample.

62 Claims, 4 Drawing Sheets

U.S. PATENT DOCUMENTS

| | | | |
|---|---|---|---|
| 4,707,450 A | | 11/1987 | Nason .................... 435/295 |
| 4,762,857 A | | 8/1988 | Bollin, Jr. et al. .......... 514/777 |
| 4,810,658 A | * | 3/1989 | Shanks et al. ............. 436/172 |
| 4,818,883 A | * | 4/1989 | Anderson et al. ....... 250/361 C |
| 4,833,075 A | | 5/1989 | Vijayalaksshmi et al. ...... 435/8 |
| 4,891,319 A | | 1/1990 | Roser .................... 435/188 |
| 4,978,504 A | | 12/1990 | Nason ..................... 422/61 |
| 4,985,631 A | | 1/1991 | Wannlund et al. |
| 5,004,684 A | | 4/1991 | Simpson et al. ............. 435/8 |
| 5,082,628 A | | 1/1992 | Andreotti et al. ........ 422/82.08 |
| 5,188,965 A | | 2/1993 | Wannlund ................. 436/165 |
| 5,258,285 A | | 11/1993 | Aegidius ................... 435/8 |
| 5,278,075 A | | 1/1994 | Stone ..................... 436/73 |
| 5,338,666 A | | 8/1994 | Monthony et al. ........... 435/34 |
| 5,358,691 A | * | 10/1994 | Clark et al. ................ 422/64 |
| 5,366,867 A | | 11/1994 | Kawakami et al. ............ 435/8 |
| 5,396,325 A | | 3/1995 | Carome et al. ............. 356/128 |
| 5,413,939 A | * | 5/1995 | Gustafson et al. .......... 436/518 |
| 5,422,075 A | * | 6/1995 | Saito et al. ................. 422/52 |
| 5,558,986 A | | 9/1996 | Lundin ..................... 435/4 |
| 5,580,785 A | | 12/1996 | Stiffey et al. ............ 435/288.7 |
| 5,589,136 A | | 12/1996 | Northrup et al. ........... 422/102 |
| 5,624,810 A | | 4/1997 | Miller et al. ................ 435/8 |
| 5,624,815 A | | 4/1997 | Grant et al. ................ 435/30 |
| 5,648,232 A | | 7/1997 | Squirrel ................... 435/34 |
| 5,650,289 A | * | 7/1997 | Wood ...................... 435/8 |
| 5,663,050 A | | 9/1997 | Bedell ................... 435/7.23 |
| 5,700,427 A | * | 12/1997 | Ghaed et al. ............... 422/52 |
| 5,760,406 A | | 6/1998 | Powers .................. 250/461.2 |
| 5,770,391 A | | 6/1998 | Foote et al. ................. 435/8 |
| 5,783,399 A | | 7/1998 | Childs et al. .............. 435/7.2 |
| 5,801,007 A | | 9/1998 | Simpson et al. .............. 435/8 |
| 5,811,251 A | | 9/1998 | Hirose et al. ................ 435/8 |
| 5,827,675 A | | 10/1998 | Skiffington et al. ........... 435/8 |
| 5,891,656 A | | 4/1999 | Zarling et al. ............. 435/792 |
| 5,902,722 A | | 5/1999 | Di Cesare et al. ............. 435/4 |
| 5,905,029 A | | 5/1999 | Andreotti et al. ............. 435/8 |
| 5,914,247 A | | 6/1999 | Casey et al. ............... 435/34 |
| 5,916,802 A | | 6/1999 | Andreotti ................ 435/287.7 |
| 5,917,592 A | | 6/1999 | Skiffington ............... 356/244 |
| 5,965,453 A | | 10/1999 | Skiffington et al. ......... 436/165 |
| 5,968,766 A | | 10/1999 | Powers .................... 435/29 |
| 6,024,923 A | | 2/2000 | Melendez et al. ........ 422/82.08 |
| 6,055,050 A | | 4/2000 | Skiffington ............... 356/244 |
| 6,103,534 A | * | 8/2000 | Stenger et al. .............. 436/63 |
| 6,187,267 B1 | * | 2/2001 | Taylor et al. ................ 422/52 |
| 6,191,847 B1 | * | 2/2001 | Melendez et al. ............ 356/73 |
| 6,200,531 B1 | * | 3/2001 | Liljestrand et al. ........... 422/52 |
| 6,325,978 B1 | * | 12/2001 | Labuda et al. ............... 422/84 |
| 6,372,511 B1 | * | 4/2002 | Silver et al. ............... 436/165 |
| 6,458,547 B1 | * | 10/2002 | Bryan et al. ............... 435/7.1 |
| 6,509,195 B1 | * | 1/2003 | De Rooij et al. ........... 436/172 |
| 6,579,722 B1 | * | 6/2003 | Collins et al. ............. 436/172 |
| 6,660,469 B1 | * | 12/2003 | Wright et al. ................ 435/4 |

OTHER PUBLICATIONS

Franks, Felix; Long–Term Stabilization of Biologicals; Bio/Technology vol. 12 Mar. 1994; pp. 253–256.

Lappalainen, Juha, et al; Microbial Testing Methods for Detection of Residual Cleaning Agents and Disinfectants—Prevention of ATP Bioluminescence Measurement Errors in the Food Industry; Apr. 27, 1999; Journal of Food Protection, vol. 63, No. 2, 2000, pp. 210–215.

Lundin, A. et al; ATP Extractants Neutralised By Cyclodextrins; Clinical Research Centre, Karolinska Institute, S–141 86 Huddinge, Sweden and BioThema AB, Strandvägen 36, S–130 54 Dalarö, Sweden; Amersham International plc, Cardiff Wales CF4 7YT, United Kingdom; pp. 399–402.

Mazzobre, M.F. et al; Combined effects of trehalose and cations on the thermal resistance of beta–galactosidase in freeze–dried systems; ; http://www.confex2.com/ift/99annual/abstracts/4344.htm; Jun. 22, 2000.

Miller, Danforth P., et al; Thermophysical Properties Of Trehalose and Its Concentrated Aqueous Solutions; Dec. 30, 1996; Pharmaceutical Research, vol. 14, No. 5, 1997; pp. 578–590.

Reilly, MJ et al; Factors Affecting The Shelf Life Of Freeze–Dried Firefly Luciferase Reagents; Biotrace Limited, The Science Park, Bridgend, Mid Glamorgan, CF31 3NA, UK; pp. 257–260.

Ribeiro, Angela R., et al; Immobilisation of Firefly Luciferase on Glass Strips as an Alternative Strategy for Luminescent Detection of ATP; Apr. 8, 1999; Luminescence Assays for Industry—Angela R. Ribeiro—Abstract; p. 1 of 1.

Velazquex, Madeline et al; Quenching and Enhancement Effects of ATP Extractants, Cleansers, and Sanitizers on the Detection of the ATP Bioluminescence Signal; Sep. 10, 1996; Journal of Food Protection, vol. 60, No. 7, 1997, pp. 799–803.

Wang, Chung–Yih et al; Interfacial Behavior of Firefly Luciferase; Department of Bioengineering, University of Utah, Salt Lake City, UT 84112, USA; pp. 99–103.

Wang, Chung–Yih et al; Purification and Preservation of Firefly Luciferase; Department of Bioengineering, 2480 MEB, University of Utah, Salt Lake City, UT 84112, USA; pp. 423–426.

Wang, CY et al; Surfactants And CoEnzyme A As Cooperative Enhancers Of The Activity Of Firefly Luciferase; Dept. of Bioengineering, University of Utah, SLC, UT 84112, USA; pp. 253–256.

Ford, Sharon et al; Improvements in the Application of Firefly Luciferase Assays: Methods in Molecular Biology, vol. 102: Bioluminescence Methods and Protocols, 1998.

Lundin, Arne; Optimised Assay of Firefly Luciferase With Stable Light Emission: Chemiluminescent and Bioluminescent Assays, 1993.

Wood, Keith, The Chemistry of Bioluminescent Reporter Assays: *Promega Notes* No. 65: 1998, p. 14.

Lewis, Ricki, Refinements in Bioluminescence Assays Expand Technique's Applications; The Scientist 8 [5]:17, Mar. 7, 1994.

* cited by examiner

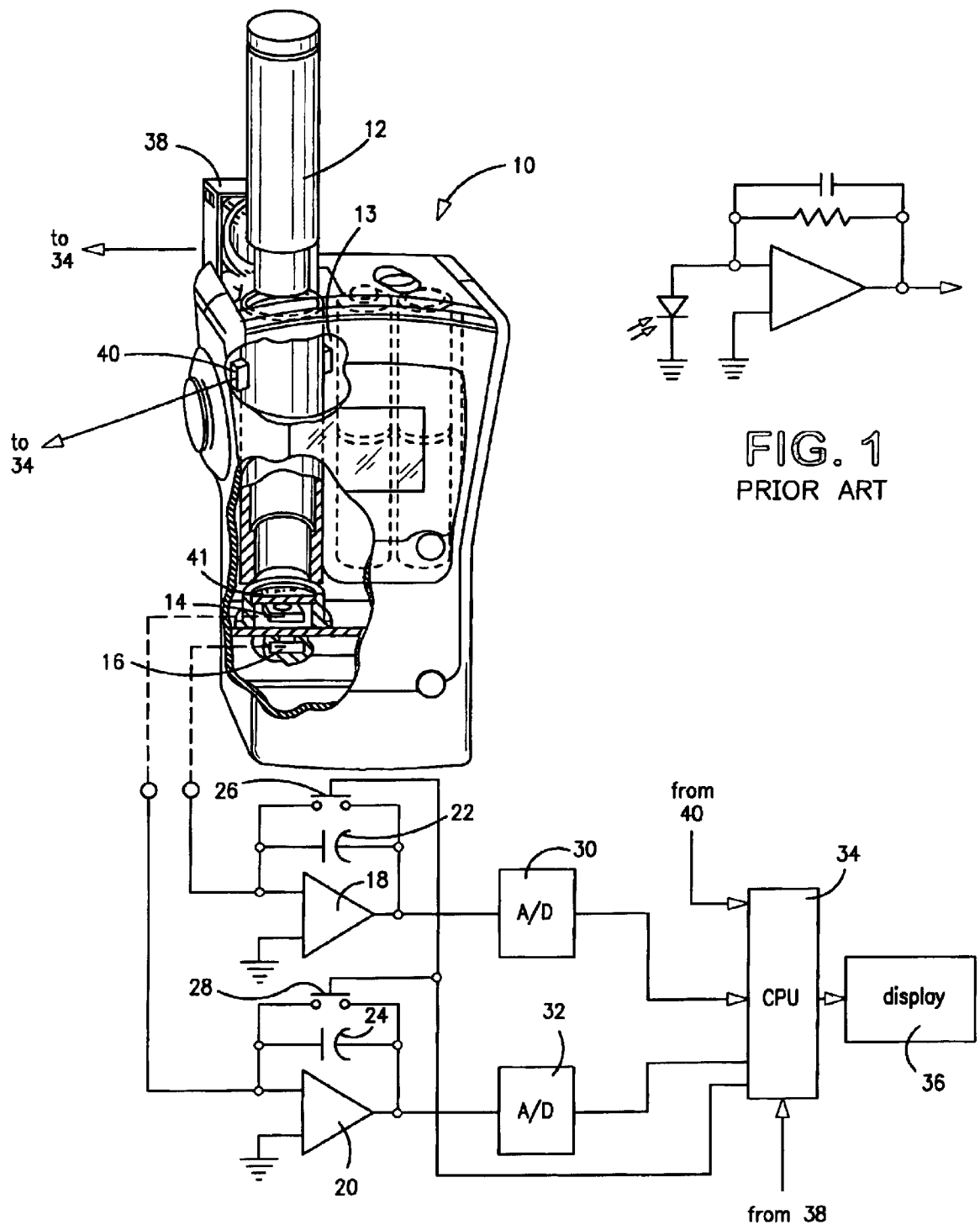

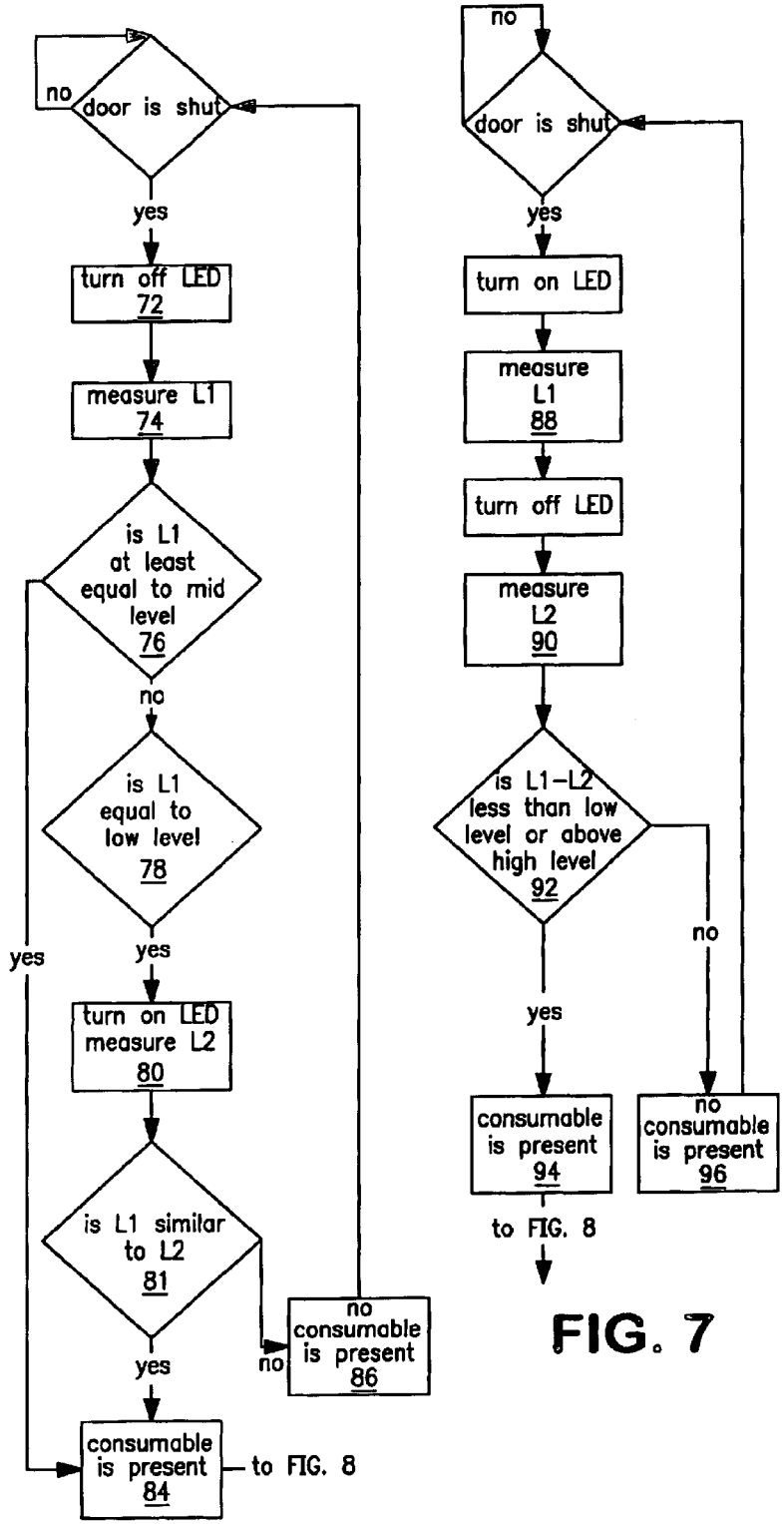
FIG. 6
FIG. 7
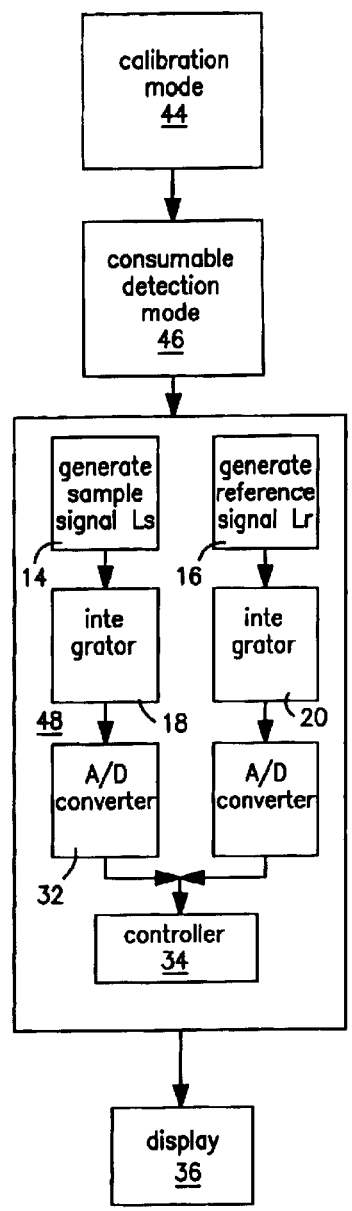
FIG. 3

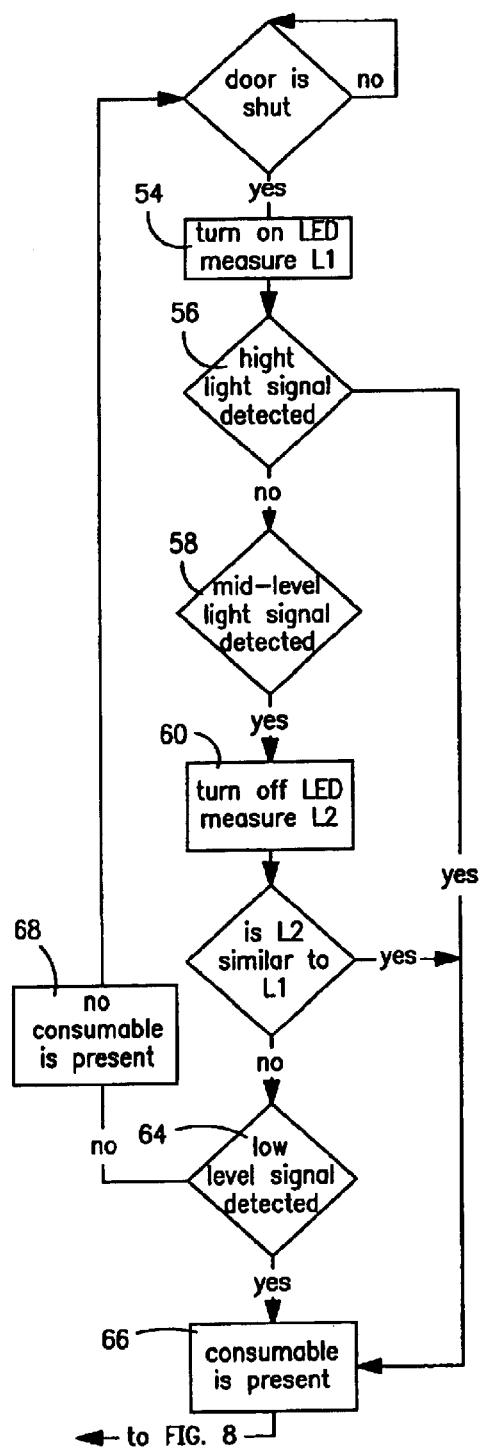
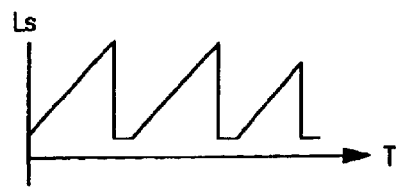
FIG. 11a
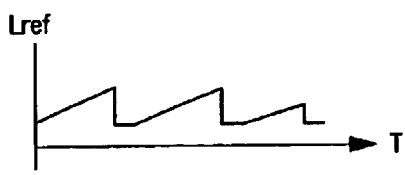
FIG. 11b
FIG. 11c
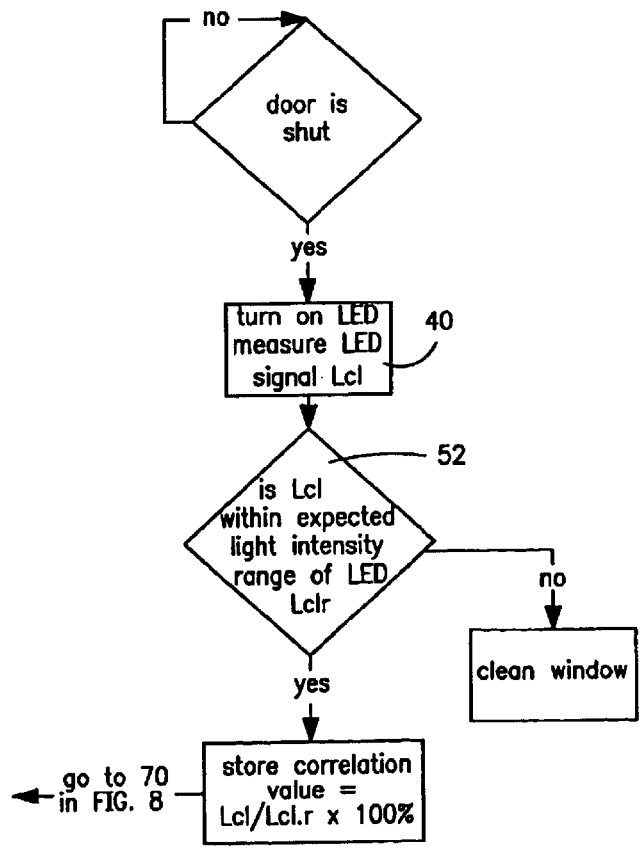
FIG. 5
FIG. 4

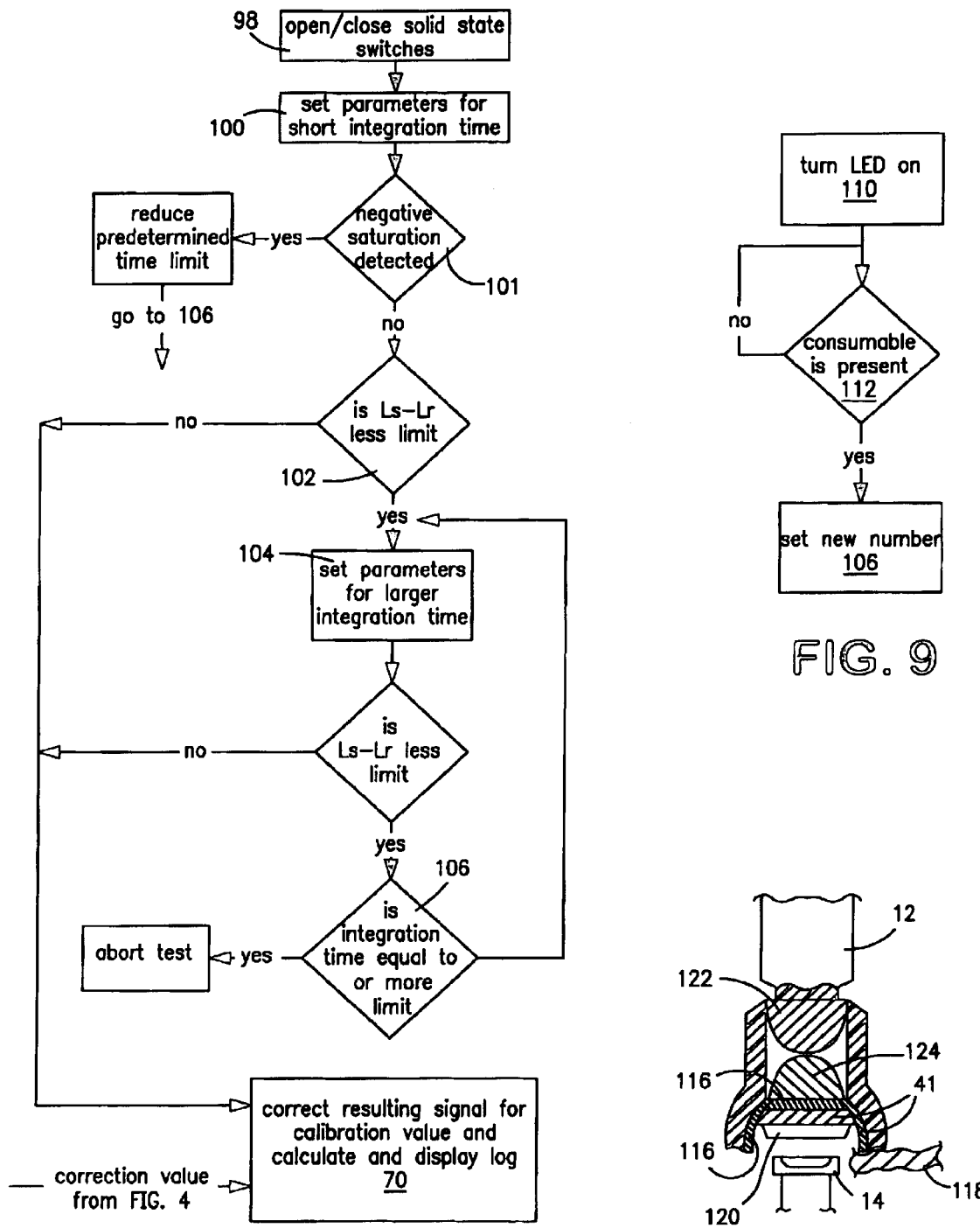
FIG. 8
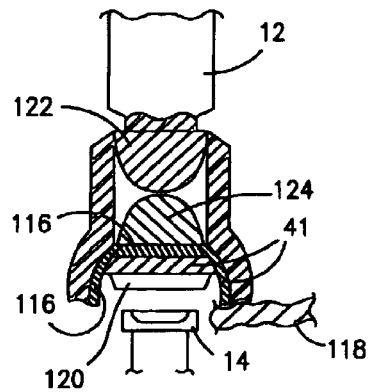
FIG. 9
FIG. 10

METHODS AND APPARATUS TO IMPROVE THE SENSITIVITY AND REPRODUCIBILITY OF BIOLUMINESCENT ANALYTICAL METHODS

PRIOR APPLICATION

I claim priority benefits under 35 U.S.C. §119(e) of U.S. Provisional Patent Application Ser. No. 60/193,974 filed Mar. 31, 2000.

FIELD OF THE INVENTION

The invention relates to techniques and apparatus for detecting light produced by a chemical reaction and known as chemiluminescence. Particularly, the invention relates to a hand-held ATP-chemiluminescence detection device used primarily in the food processing and food preparation industries for assessing cleanliness of various surfaces.

BACKGROUND OF THE INVENTION

Sanitary concerns as well as federal and state regulations in food processing and food preparation industries necessitate a device capable of rapidly and efficiently detecting various test samples from materials or surfaces. Various test apparatuses and test methods have been developed for that purpose. For example, it is widely desirable to determine or to test through quantitative and qualitative tests food, such as meat products, fruit, vegetables, and to detect for alkaline phosphates, salmonella, drugs, and antibiotics, such as; for example, various bacteria and pathogenic combinations, either in materials or on the surface of materials, or both.

The present commercial tests for the detection of ATP-luciferase reaction are generally directed to a chemiluminescence test, which ordinarily employs premeasured and prepackaged separate test reagents mixing with the test sample to produce chemiluminescence. Accordingly, the count corresponding to the concentration of the ATP, which is determined by measuring or counting of the chemiluminescence, is compared against certain accepted control standards, or a threshold of a control standard.

Photomultiplier consumable-based detectors have been typically used to monitor the ATP-luciferase reaction. A photomultiplier consumable or PMT, capable of responding on an individual photon-by-photon basis amplifies low-level light intensity generated by chemiluminescence. As any light amplifying device, PMT is a delicate device that is not particularly suited for use by an unsophisticated user typically employed in food processing and food preparation industries and is bulky and costly requiring employment of a complicated manufacturing process.

Another device capable of generating an output current in response to low-level light signals is a photodiode, which is known to generate currents substantially lower than PMT. To convert currents from PMT into a useful electrical representation, an analog front-end circuit, such as the transimpedance amplifier, has been employed in devices used to measure chemiluminescence. As shown in FIG. 1, a typical transimpedance amplifier uses resistance to provide a real time linear representation of the light source. Input current generated by a photo-detector flows through the feedback resistor, $R_F$, to create a proportional output voltage $V_O = -I_{IN} R_F$. Accordingly, since $R_F$ determines the transimpedance gain (amplification), very large values (gigaohm) of the feedback resistance $R_F$ are required to measure small signal input current. However, transimpedance amplifiers with such high values of the feedback resistor are notorious for production problems—since the resistor and circuit board must be extremely clean to prevent stray feedback paths that otherwise will lower the gain of the amplifier, which can be detrimental for devices used to detect low level signals generated as a result of chemiluminescence. Also, to maintain the desirable cleanliness is even more difficult in the food production and food processing industries where such devices are employed.

Also, the dynamic range of the transimpedance amplifier is limited unless gain switching is employed. Such gain switching includes a plurality of feedback resistors having different values. The higher the resistance value is, the higher the gain of the amplifier. The low photocurrent levels prevent the use of solid-state relays. Therefore, gain switching requires reed relays, which would make a device employing this amplifier less rugged because any mechanical structure is easily worn out.

To reduce the wear of the relays, the transimpedance amplifier makes the measurement at the "typical" gain level. This approach increases the time spent on the measurement, which is undesirable because the specifics of the food processing industry require that tests be performed frequently and in great number.

Furthermore, the transimpedance amplifier and reed relays require separate supply voltages necessitating separate dc-to-dc converters for battery operation, which leads to increased dimensions of a testing device utilizing the transimpedance amplifier. Discrete samplings used in the testing device means momentary high light levels because of the direct exposure to room light. As a consequence, the charge is collected at a capacitor which is necessary to be discharged before the next test is conducted. Thus, a decay rate for the impedance amplifier corresponds to the fixed RC time constant making the user wait before a subsequent test can be performed.

The high front-end amplification typically makes a measuring system sensitive to environmental changes, particularly temperature drift. Typically, acquiring a baseline signal immediately before the desired signal, and subtracting the baseline signal measurement from the signal measurement correct such baseline shifts. However, this technique brings reliable results only if the baseline change is slowly varying, which is not the case with the food processing and food preparation industries where for example a cold storage room may be located next to a kitchen thus providing substantial temperature drift.

Still another measurement technique based on the photodiode detection includes a baseline measurement immediately before and after the desired signal measurement, and an average baseline signal is then subtracted from the signal measurement. Similarly to the above-discussed method, this correction can work well as long as the change in the baseline with time is nearly constant.

Finally, by monitoring the baseline signal it is sometimes possible to account for a non-uniform change in the baseline by fitting the change in the baseline to a known response function, and subtracting the calculated baseline from the measured signal.

Such procedures can only work if there is a known time period in which to acquire one or more baseline readings.

The technique of measuring the baseline before/after the sample measurement period requires the use of a shutter or some other means of ensuring that a sample is not resulting in a photodiode current, which has been associated with a few problems in case of a hand-held device. The currents generated when the shutter moved detrimentally affected the final measurement. Furthermore, both the shutter and a motor for actuating the shutter were too big to fit in the desired package. Also, the power requirements of the motor would have added substantially to the power drain placed on the batteries. Finally, the use of shutter assembly contributed to the relatively high cost and the poorer reliability.

It is known that many photodecting transducers used for the detection of luminescence are very sensitive to static charge; for instance, static charges seen when a sample consumable is inserted into the sample compartment. Conventionally, a sample compartment of known devices must be made of a conductive material or some other means must be provided to drain static charge from the sample consumable. In most cases, it is difficult to achieve the required intimate contact between the sample compartment and a conductive wall of the sample compartment to quickly drain the static charge. In other cases, it is difficult to use a conductive sample compartment, which makes it very difficult to ensure that any static charge retained on the sample consumable does not influence the signal output.

Also, a shutter is used to shield a photodiode from direct exposure to high light levels which can damage the detection circuitry and often will increase noise. Unfortunately, any static charge or potential difference on a shutter mechanism will result in a transient signal as the shutter is moved across the photodiode. Given the low-level of the photogenerated currents that must be detected, nonconductive or partially conducting surface films on the shutter can cause associated capacitances and potential differences that result in large transients that may be much larger than the photogenerated currents.

Finally, particularly in hand-held instruments of the described-above type it is difficult to fully shield the high sensitivity detection system completely to reduce spurious noise effects. This is a particular acute problem along the optical path, since most optically transparent material are nonconductors.

It is, therefore, desirable to have a hand-held device provided with a photodiode-based detection system for monitoring the ATP-luciferase reaction to provide a cost-efficient hand-held device. Furthermore, it is desirable to provide the hand-held device wherein the photodiode-based detection system for monitoring the ATP-luciferase reaction is coupled with a switched integrator to overcome the drawbacks associated with the transimpedance amplifier. Also desirable is the hand-held device wherein negative effects of static charge on a photodiode-based detection system are minimized.

SUMMARY OF THE INVENTION

In accordance with the invention, a hand-held assay device has a photodiode transducer, which is capable of generating an output current in response to low-level light signals generated by the ATP-luciferase reaction, and a switched integrator, which integrates a sample signal corresponding to the low-level input current for a user-determined period.

To increase the precision of detection and to automatically compensate for environmental changes, such as temperature and humidity, the inventive assay device further utilizes two channels of an available switched integrator to simultaneously measure both a reference signal indicative of the environmental changes and the sample signals. Thus, in addition to the sample signal generated in response the chemiluminescence by the sample photodiode, a reference photodiode, blocked from light detects the dark current due to the environmental changes and generates the reference signal. Since the photodiodes are in close proximity, the effects of these environmental changes are canceled providing excellent baseline correction even when the system is subjected to rapid temperature swings. Any correlated noise on the photodiodes will also cancel out.

In accordance with another aspect of the invention, the assay device can provide a self-calibrating test, wherein a LED generates a signal on demand, which is measured by the first photodiode mounted immediately below transparent window, indicating the desired cleanliness of the window.

According to still another aspect of the invention, the assay device has electronics allowing an automatically determine integration time period to be used so that a measurement is made before the integrators reach the state of saturation.

It is therefore an object of the invention to provide a hand-held assay device that makes possible the rapid detection through chemiluminescence of the presence of ATP on a surface.

Still another object of the invention is to provide an assay device that is operated by unskilled operators under the relatively harsh field environment of institutional food service preparation services, health care providers and the like.

Still another object of the invention is to provide an assay device having a cost efficient detection system that includes at least one photodiode capable of detecting the chemiluminescence signal.

A further object of the invention is to provide an assay device having a system for amplifying low-level signals generated by a photodiode in response to the detection of the chemiluminescence and including at least one switched integrator.

Still another object of the invention is to provide an assay device capable of automatically compensating for changes in detector baseline, independent of environmental changes and effect these change have on a front-end switched integrator.

Yet another object of the invention is to provide an assay device capable of automatically evaluating the cleanness of its transparent parts before an analytical test has been conducted.

A further object of the invention is to provide an assay device in which noise generated by static charge is minimized.

BRIEF DESCRIPTION OF THE DRAWINGS

The above and other objects, features and advantages will become more readily apparent from the following specific description accompanied by the following drawings, in which:

FIG. 1 is a transimpedance amplifier used in the prior art handheld devices for detecting chemiluminescence.

FIG. 2 is a perspective view of an assay device in accordance with invention shown with an inventive detection circuit.

FIG. 3 is a flow chart illustrating an operation of the device of FIG. 2.

FIG. 4 is a flow chart illustrating a calibration mode of the device shown in FIG. 2.

FIG. 5 is a flow chart illustrating a consumable-detection mode in accordance one embodiment of the device of FIG. 2.

FIG. 6 is a flow chart illustrating another embodiment of the consumable-detection mode of the device shown in FIG. 2.

FIG. 7 is a flow chart illustrating another embodiment of the consumable-detection mode of the device shown in FIG. 2.

FIG. 8 is a flow chart illustrating an analytical mode employed in the device shown in FIG. 2.

FIG. 9 is a flow chart of a manual mode of the device shown in FIG. 2.

FIG. 10 is a sectional view of a transparent window located along an optical path between a sample chamber and electronics of the device shown in FIG. 2.

FIGS. 11A–11C graphically illustrate a measuring technique employed in the device of FIG. 2.

DETAILED DESCRIPTION OF THE DRAWINGS

Referring to FIG. 2, a hand-held assay device 10 includes a consumable 12 removably inserted in a sample compartment 13 and containing a sample which as a result of ATP-luciferase reaction can generate a low level chemiluminescence, as explained in patent application Ser. No. 09/821,148, now U.S. Pat. No. 6,548,018 B2 granted Apr. 15, 2003, which is owned by the same assignee and fully incorporated herein by reference.

In accordance with the invention, detection of this low-light level chemiluminescence is detected by a photodiode 14 placed in a housing of the device in the close proximity of the sample. The photodiode is sensitive to femtoamp-level currents ($10^{-15}$ amps) detected by a system which is fronted by a switched integrating amplifier or switched integrator 18. The switched integrator reduces the analog circuitry, which is characteristic of the transimpedance amplifier, and brings digitization process closer to the photodiode placed across the inputs of the switched integrator.

As shown in FIG. 2, the switched integrator 18 is used with a fairly low integration capacitor 22 (10–500 pF) in a feedback loop. This is combined with a reset solid-state switch 26. The switch integrator operates by collecting the photodiode output charge on the integration capacitor 22 while the reset switch 26 is open. Once it is closed, the output of the switched amplifier equals to zero volts. When this is accomplished the reset switch is open again starting the process all over again. The analog gain of this input stage is changed with values of the integration capacitor 22, or preferably, with changing the integration time, defined as the time duration during which the reset switch is open.

The digitized signal is further sent to a controller, which is typically a microprocessor. If the integrated value of the signal is equal to or greater than the reference or threshold value after applying the necessary corrections, a display 36 indicates the presence of the microorganisms in a suitable form. If, however, the output signal has not quite reached a measurable value, the integration time during which the reset switch is open can be incrementally increased by software executing on the microprocessor, as will be explained below.

In comparison with the transimpedance amplifier, the switched integrator has an extended dynamic range of 10^8 and does not require mechanical relays for switched gains. Furthermore, the switched integrator does not require a separate +/− voltage supply for the operational amplifiers that would be used for a low-noise/high gain transimpedance amplifier.

With the single switched integrator 18, analog/digital converter 30 and the single photodiode, adequate detection requires that each measurement be integrated for up to 30 seconds. An extended measurement period renders a device equipped with the photodiode difficult to use, because the user is typically required to provide frequent tests in a short period of time. In addition, since the baseline is changing during the measurement period, the long measurement period makes it more difficult to ensure that the baseline measurement will correctly estimate the baseline level during the signal measurement, particularly since the observed change is not unidirectional.

To make the measurement of the chemiluminescence less sensitive to the environmental changes, a second or reference photodiode 16 is placed in close proximity of the first photodiode 14. However, this photodiode 16 is reliably shielded from any source of light including chemiluminescence light and generates an input current primarily corresponding to environmental changes. As long as baseline and signal photodiodes 16, 14, respectively, are closely positioned, any environmental changes, such as temperature and correlated noise, can be cancelled. Thus, $Lres=(Ls+T°+Ncorr)-(Lref+T°+Ncorr)=Ls-Lref$, wherein Ls is an integrated signal generated by the first photodiode 14 and integrated by the integrator 18, and Lref is an integrated signal generated by the photodiode 16 and integrated by an integrator 20.

The embodiment including two photodiodes provides much better detection than a single photodiode. However, there are some applications where the best performance is not needed and thus the single photodiode structure can be successfully employed.

The concept illustrating the two-photodiode structure is shown in FIGS. 11A–11C, wherein FIG. 11A illustrates the signal from the photodiode 14 integrated by the switched integrator in response to the chemiluminescence. FIG. 11B illustrates the integrated signal generated in response to the temperature swing by the photodiode 16, and FIG. 11C shows the combined integrating resulting signal Lres. This signal accounts for the changes in the light signal caused by the signal corresponding to the temperature, humidity, mechanical impact and the like drift.

Structurally, the integrator 20 is identical to the previously disclosed integrator 18 and includes an integrator feedback capacitor 24, a reset switch 28 and a respective A/D converter 32. The measurement of the baseline and signal inputs are simultaneously processed during the same integration time and integrated outputs of the switched integrators are combined in the controller 34, wherein the baseline output signal is subtracted from the signal output signal, as seen in FIGS. 2 and 3.

The overall operation of the device, as shown in FIG. 3, includes an initialization or calibration mode 44, wherein transparency and/or cleanliness of components forming a light path are determined. The device further has a consumable-detection mode, wherein the presence of the consumable 12, which is used to swipe the surface for collecting a sample to be tested on ATP or other entity, in the sample compartment is verified at 46. Finally, the device has an analytical or operation mode 48, wherein the sample is tested on ATP. Particularly, the sample and reference signals (Ls, Lref) corresponding to currents generated by photodiodes 14, 16, respectively, are integrated by integrators 18 and 20, digitized in 32 and inputted in the controller 34. The controller has software for subtracting the reference signal from the sample signal. If the resulting signal is at least equal to the threshold stored in a memory of the controller, the display 36 informs the operator about the presence of ATP. The integration period will be increased if the resulting signal is lower than the reference value in accordance with a flow chart shown in FIG. 8.

Alternatively, a subtraction circuit can be implemented before the signals are fed into the microprocessor. However, being able to read the individual digitized signals prior to the subtraction provides some signal processing advantages, such as an ability to make decisions based on individual signal/baseline levels.

Referring to FIGS. 1 and 4, the calibration mode is shown. To provide a reliable measurement of ATP, optical components, such as a transparent window 41 (FIGS. 1 and 10) that locates along the light path and separates the consumable 12 from the photodiode 14, have to be clean within the expected intensity of a source of light, such as an LED 40 mounted in the sample compartment. Detection of a signal emitted by the LED is analogous to the technique employed for the ATP detection and is performed by a combination of photodiodes and switched integrators. The calibration mode begins with turning on the LED 40 generating a signal, which has the expected LED intensity range, at powering up the device. An integrated value of a resulting signal processed by the controller is compared with the reference value (Lref) set and stored in the memory of the controller during a manufacturing stage at 52. If the cleanliness signal L is within the expected range of the LED intensity, the device is ready for further operations. A correction value indicative of the relative cleanliness of the window is stored for final adjustment of a measured ATP signal at 70 (FIG. 8). If the cleanliness signal, which appears on the display, indicates that the window is soiled beyond the range, the user is required to clean the window before the device will be ready to conduct the analytical test.

Furthermore, the analytical test for detecting ATP cannot be performed unless the presence of the consumable is verified, as shown in FIG. 5. Initially, the LED is on, as indicated by 54, and the signals from the photodiodes 14 and 16 are integrated, digitized and inputted in the microprocessor 34 where a resulting signal $L_1$=Ls−Lr is measured. If the resulting signal exceeds a level above the expected LED intensity range at 56, which is equal to $NL_{led}$, wherein $L_{led}$ is the stored LED reference value, it means that this signal is emitted by a high-ATP sample which can only be contained in the consumable which has been inserted in the sample compartment, as shown at 66.

If mid-range light level is detected at 58, which is within the range of the expected LED intensity and similar to the stored value of the LED, the consumable might be present. To verify its presence, software executing on the microprocessor turns the LED off at 60, provides a measurement of a resulting consumable signal $L_2$ and, if this signal is substantially the same as $L_1$, then the consumable is present, as shown at 66.

If low light level is detected with the LED on at 64, the consumable is blocking the beam. Finally, if the resulting signal $L_1$−$L_2$ is below the low-level light intensity, then the consumable has not been inserted, as indicated at 68, and a signal that has been detected corresponds to a dark current in the reference photodiode 16.

Alternatively, as shown in FIG. 6, the consumable detection mode has the LED off at 72. If the resulting signal $L_1$ measured at 74 has the high or mid-light level, as shown at 76, the ATP is present at 84.

If the detected signal substantially corresponds to the low-light level shown at 78, which is consistent with the dark current generated by photodiode 16 dark, a sample might be present. To verify the presence of the consumable, software executing on the microprocessor turns on the LED at 80 to measure a resulting signal $L_2$ at 80. If the $L_2$ signal is similar to $L_1$, as indicated at 81, then the consumable is present. If the low level has not been detected, there is no consumable in the sample compartment, as shown at 86.

A particularly simple embodiment, wherein the presence of the consumable is verified, is shown in FIG. 7 where software executing on the microprocessor first turns on the LED and measures a first $L_1$ at 88 in accordance with the technique explained above. Then the LED is turned off at 90 to provide a measurement of the second resulting signal $L_2$, and if the L=$L_1$−$L_2$ higher than an upper limit or lower than a lower limit, as indicated by 92, the consumable is present at 94. Otherwise, the analytical test will be aborted, as indicated by 96. The procedures disclosed in reference to FIGS. 5–7 may be continually performed before conducting the analytical test until the consumable is detected.

Alternatively to optical detection of the consumable, as disclosed above, it is possible to use a mechanical microswitch to provide the detection mode. In this case, the microswitch is strategically mounted in the sample compartment to be in direct contact with the insertable consumable. Obviously, actuation of the microswitch indicates the presence of the consumable. However, advantage of optical detection is that a mechanical microswitch would be much easier to contaminate, and then more difficult to seal.

After the initialization and consumable detection modes have been completed, the device is ready to conduct the analytical test, as shown in FIG. 8. The analytical mode is directly dependent on how rapidly ambient parameters change. Under normally changing conditions, the analytical test first includes discharging photodiode charge accumulated on the feedback capacitors, which detrimentally affects a measurement of ATP. This is attained by software executing on the microprocessor which closes/opens integration switches (26, 28) at least once at 98, but if necessary more than once. Initially, a short integration time, for example 0.5 msec, is set at 100. If the resulting signal Lres=Ls−Lr is less than the predetermined threshold, as shown at 102, a larger integration time is set at 104. This sequence continues unless a satisfactory quantity of ATP is determined. However, an integration period is continuously controlled not to exceed a predetermined value at 106, for example 5 seconds. At this point the test is completed.

However, if the environmental changes are rapid, the switched integrator can reach a saturation mode substantially sooner than the 5-second limit. In that case, the shorter integration time result can be used to predict that integrator saturation could occur at next predetermined integration time. Note, the expected baseline is known. This is particularly true at short integration time because it is difficult to expect any change to achieve a critical level within, for example, a 0.5 msec period. Then if the 0.5 msec integration time signal is below baseline to the extent that 10 times that negative offset would be less than zero-than obviously, 5 sec integration time measurement cannot be made. As a result, software executing on the controller can dynamically change the integration time limit from 5 seconds to, for example, 2 seconds, as shown at 101.

The threshold is selected such that the sample-to-sample variation is dominated by the process of sampling and mixing instead of being defined by the signal-to-noise ratio of the electronics. In other words, the threshold is selected to be N times greater than the empirically determined inherent noise of the electronics. Specifically the minimum counts at any integration time corresponds to about a 1% of relative standard deviation (RSD), while sampling/mixing will cause measured precision to be more than 5%. Thus, dynamically changing the integration time in accordance with software executing on the microprocessor allows the device to operate with the best possible signal-to-noise ratio for the given environmental conditions including temperature, humidity, external shocks and the like.

After the ATP has been detected, the signal representing it is corrected at 70 in accordance with the correction value and a logarithmic number of the corrected signal value is calculated and displayed.

Note, none of the modes can be performed unless a door 38 (FIG. 1) allowing access to the sample compartment 13 is closed. Software executing on the microprocessor is able to verify the closed state of the door. Furthermore, the device will not operate even if a small hole is formed in the lid. Obviously, during the first detection of light coming through the hole, the device will read a signal as the one emitted by a high-ATP sample. However, during the next measurement indicating the high-ATP sample, the device will warn a user to check if the lid is damaged.

FIG. 9 illustrates a manual mode of the device, wherein a user, based on local requirements, is able to set a new limit for indicating the presence of ATP. Typically, if the measured quantity of ATP exceeds the threshold number stored in the memory of the controller and assumed to be indicative of the ATP, the measured number appears on the display. However, local requirements that can be different from a criteria used during the manufacturing stage may necessitate a user to choose a different threshold number, which will be indicative of the ATP. To do so, the microprocessor turns on the LED at 110 in response to powering up the device. After verifying the absence of the consumable at 112, the user using the menu can set a desirable number at 106. If a given measurement meets the newly set number, a check mark indicative of the sufficient quantity of ATP along with the number appear on the screen.

Similarly to the environmental changes, static charges, such as those seen when the sample consumable is introduced in the compartment, negatively affect the inventive detection system. The highly current-sensitive photodiode 14 of the present invention is also sensitive to spurious static charges. Also, the inventive structure makes it very difficult to use a metal sample compartment, semi-conductive plastics, although available, still have a surface resistance of about $10^{\wedge 6}$ ohms/sq making it likely that this resistance will not eliminate signal transients due to the static charge on the sample consumable.

To minimize the effect of these charges, the window 41, as shown in FIG. 10, is made of glass has its side, which faces the sample compartment, coated with a transparent conductive coating 116. The coating is in contact with an electro-conductive chassis 118 of the device to form and act as a Faraday cage. Preferably, this coating is indium tin-oxide (ITO). A bottom side of the window is coated with a layer 120 acting as a bandpass filter to limit the light striking the photodiode 14.

It is foreseen within the scope of this invention to place the ITO on the window of photodiode, since typically the case of photodiode is conductive, and it ensures a dissipation path of any transferred charge to the ground.

Also, it is possible to cover only the bottom side of the window with the ITO, whereas the opposite side is provided with a band pass or band limited filter. Note, the filter can be a coating or is a made of a whole body. In this case, a wavy washer needs to be interposed the photodiode 14 and the coating to provide electrical contact between these components.

Thus, discharge effects resulted from closing/opening of the integration switches and having the ITO coating eliminate the need in a mechanical shutter. This, in turn, generates significant cost savings while also increases the reliability of the instrument through the elimination of a complicated mechanical assembly, such as the shutter.

Although the reference photodiode effectively eliminates the effects the environmental changes, it has been found that an optic is still required between the sample photodiode and the consumable, because the consumable is often not at thermal equilibrium with environment. This necessitates a larger distance between the sample photodiode and the transparent window. On the other hand, the increased distance affects an optical path. Clearly, the closer the source of light to the transparent window and, therefore, to the photodiode, the less distortion of the light beam. In one embodiment of the present invention, shown in FIG. 10, this dichotomy is reconciled by introducing a combination of two plano-convex lenses 122, 124 between the consumable 12 and the transparent window 41.

Although the invention has been described with reference to a particular arrangements of parts, features and the like, these are not intended to exhaust all possible arrangements or features, and indeed many other modifications and variations will be ascertainable to those of skill in the art.

What is claimed is:

1. A hand-held assay device for measuring the presence of a sample generating chemiluminescence, comprising:

a housing with a closeable door for enclosing the sample in a sample compartment of the housing so that the sample is inside the housing in the absence of a source of light from outside of the housing when the door is closed;

a first light sensor inside the housing for generating a sample signal in response to detecting the chemiluminescence;

a second light sensor inside the housing shielded from the chemiluminescence and generating a reference signal;

a controller inside the housing receiving the sample signal and the reference signal, wherein the controller outputs a resulting signal indicative of the sample and determined as the difference between the sample and reference signals; and software executed on the controller for determining the presence of light from outside the housing when the door is open and for generating a warning signal in response to the detection of the light, wherein the controller prevents the device from operating further unless there is an absence of a source of light from outside of the housing.

2. The hand-held assay device defined in claim 1, further comprising a pair of analog to digital converters digitizing the sample and reference signals, respectively, and software executed on the controller for subtracting the digitized reference signal from the digitized sample signal.

3. The hand-held assay device defined in claim 1, further comprising software executed on the controller for calculating a logarithmic number of the resulting signal and a display for displaying the calculated logarithmic number if calculated resulting signal exceeds a threshold value.

4. The hand-held assay device defined in claim 1, further comprising a transparent window in the sample compartment upstream from the first light sensor and spaced from the door, the transparent window for transmitting the chemiluminescence generated by the sample to the first light sensor.

5. The hand-held assay device defined in claim 1, further comprising software executed on the controller for measuring first and second values of a signal processed by the controller with a LED on and off, respectively, software for subtracting second value from the first value, and software for outputting the signal indicative of the absence of the consumable if the difference is between a high-level and a low level of the predetermined range stored in the memory.

6. The hand-held assay device defined in claim 1 wherein the controller is a microprocessor having a memory which stores a sample threshold value, the hand-held device further comprising software executing on the microprocessor for closing solid state switches for a controllable integration time to provide the integrated values of the sample and reference signals corresponding to the duration of the closed state of the solid state switches, and software for comparing a value representing the resulting signal to the sample threshold value to determine the sample if the resulting signal is at least equal to the sample threshold value.

7. The hand-held assay device defined in claim 6, further comprising software executed on the controller for incrementally increasing the integration time if the resulting signal is less than the sample threshold value.

8. The hand-held assay device defined in claim 1, wherein the first and second light sensors are photodiodes, the hand-held device further comprising sample and reference switched integrators, each connected in series with the respective one of the photodiodes and outputting integrated values of the sample and reference signals received by the controller, the reference signal being generated in response to environmental changes selected from the group consisting of temperature, humidity, external shocks and a combination thereof.

9. The hand-held assay device defined in claim 8, wherein each of the integrators is provided with a respective integration bypass capacitor and a solid state switch connected in parallel to one another to provide the integrated values of the sample signal and the reference signal.

10. The hand-held assay device defined in claim 8, further comprising software executed on the controller for closing/opening solid state switches before determining the resulting signal indicative of the sample presence to short integration feedback capacitors for discharging accumulated photodiode charge.

11. The hand-held assay device defined in claim 1, wherein the controller has a detection mode for a consumable for generating the chemiluminescence in the presence of the sample, wherein software is executed on the controller for detecting whether a signal inputted in the controller is within a predetermined range of intensity, which has low, mid and high levels and for determining if this signal is indicative of the presence of the consumable in the sample compartment.

12. The hand-held assay device defined in claim 11, further comprising software executed on the controller for turning a LED on, and software executed on a microprocessor for outputting an integrating value of the signal indicative of the presence of the consumable if the integrating value is at least equal to the stored $L_{led}$ reference value and the high level exceeding $NL_{led}$, wherein $L_{led}$ is the stored LED reference value and N is a predetermined integer.

13. The hand-held assay device defined in claim 11, further comprising software executed on the controller for turning a LED off if the value of the signal inputted in the controller has been determined to be at least equal to the mid-level but less than the high level of the predetermined range with the LED on, wherein the mid-level corresponds to a stored LED reference value, software executed on the controller for determining a new integrated value of the signal detected in response to turning the LED off, and software executed on the controller for comparing the integrated values L1, the difference between the sample signal and the reference signal, and L2, a resulting consumable signal, with the LED on and the LED off, respectively, to display the signal indicative of the presence of the consumable if these integrated values are substantially the same.

14. The hand-held assay device defined in claim 11, further comprising software executed on the controller for comparing the signal inputted in the controller with a LED off to the low level of the predetermined range and displaying a warning signal indicative of the absence of the consumable if the integrated value of the inputted signal is below the low level.

15. The hand-held assay device defined in claim 11, further comprising software executed on the controller for turning a LED off, said signal being indicative of the presence of the consumable in response to determining an integrated value of the signal if the determined value is at least equal to the mid-level of the predetermined range.

16. The hand-held assay device defined in claim 15, further comprising software executed on the controller for determining whether the signal is at least equal to the low level of the predetermined range, software executed on the controller for turning the LED on in response to detection of the low level, software executed on the controller for determining an integrated value of the signal after the LED has been turned on, and software for comparing the values of the resulting signal with the LED off and on, respectively, to display the signal indicative of the presence of the consumable if the determined values are substantially the same.

17. A hand-held assay device for measuring the presence of a sample generating chemiluminescence, comprising:
   a housing for enclosing the sample in a sample compartment so that the sample is inside the housing in the absence of a source of light from outside of the housing;
   a first light sensor inside the housing for generating a sample signal in response to detecting the chemiluminescence;
   a second light sensor inside the housing shielded from the chemiluminescence and generating a reference signal;
   a controller inside the housing receiving the sample and reference signal to output a resulting signal indicative of the sample and determined as the difference between the sample and reference signals, wherein the controller is a microprocessor having a memory which stores a sample threshold value;
   software executing on the microprocessor for closing solid state switches for initiation of a controllable integration time to provide the integrated values of the sample and reference signals corresponding to the duration of the closed state of the solid state switches;
   software for comparing a value representing the resulting signal to the sample threshold value to determine if the resulting signal is at least equal to the sample threshold value;
   software executed on the controller for incrementally increasing the integration time if the resulting signal is less than the sample threshold value;
   software executed on the controller for completing the determination of the sample upon reaching a predetermined integration time limit stored in the memory; and software executed on the controller for detecting negative saturation of a switched integrator due to a rapid environmental change and for setting an integration time limit shorter than the predetermined time limit.

18. A hand-held assay device for measuring the presence of a sample generating chemiluminescence, comprising:
   a housing for enclosing the sample in a sample compartment so that the sample is inside the housing in the absence of a source of light from outside of the housing;
   a first light sensor inside the housing for generating a sample signal in response to detecting the chemiluminescence;
   a second light sensor inside the housing shielded from the chemiluminescence and generating a reference signal;
   a controller inside the housing receiving the sample and reference signal to output a resulting signal indicative of the sample and determined as the difference between the sample and reference signals;
   an LED turned on in response to powering up the device to emit a beam of light extending along a path; and
   a transparent window along the path between the LED and the first light sensor, the controller having a calibration mode, wherein the cleanliness of the window is controlled in response to a signal generated by the first light sensor which struck by the beam from the LED.

19. The hand-held assay device defined in claim 18, further comprising software executed on the controller for turning the LED on in response to powering up of the hand-held device, software executed on controller for measuring the signal representing light intensity of the light beam penetrating through the transparent window, and a comparator for providing a calibration value if the measured signal is within an expected intensity range of an LED reference signal stored in the memory.

20. The hand-held assay device defined in claim 19, further comprising software executed on the controller for adjusting the resulting signal indicative of the sample presence for the calibration value.

21. The hand-held assay device defined in claim 19 wherein the transparent window is made from glass.

22. The hand-held assay device defined in claim 21 wherein one of the opposite sides of the window is coated with a coating of an optically transparent, conductive material to minimize the direct injection of charge during introduction of the sample into the sample compartment.

23. The hand-held assay device defined in claim 22 wherein the coating is indium tin-oxide, ITO, placed on the side of the window, which faces away from a first photodiode, to form with a chassis of the hand-held device a discharging element acting as a Faraday cage, the opposite side of the window being covered with a filter to limit the light striking the first photodiode.

24. The hand-held assay device defined in claim 21 wherein the window is made from a coated glass to serve as a filter selected from the group consisting of a band pass filter and band-limited filter.

25. The hand-held assay device defined in claim 22 wherein the coating is placed on a side of the window facing a first photodiode, whereas the other side of the window is covered with a filter.

26. A hand-held assay device for measuring the presence of a sample generating chemiluminescence, comprising:
   a housing for enclosing the sample in a sample compartment so that the sample is inside the housing in the absence of a source of light from outside of the housing;
   a first light sensor inside the housing for generating a sample signal in response to detecting the chemiluminescence;
   a second light sensor inside the housing shielded from the chemiluminescence and generating a reference signal;
   a controller inside the housing receiving the sample and reference signal to output a resulting signal indicative of the sample and determined as the difference between the sample and reference signals; and
   a transparent window in the sample compartment upstream from the first light sensor and a door spaced from the transparent window wherein a LED is mounted in a peripheral wall of the sample compartment and spaced from the transparent window, wherein a consumable for generating the chemiluminescence in the presence of the sample, which has been used to swab a surface to collect the sample to be tested, is removably inserted into the sample compartment to bring the sample to the window.

27. The hand-held device defined in claim 26, wherein the consumable is positioned in the sample compartment to block the beam of light emitted by the LED.

28. A hand-held assay device for measuring the presence of a sample generating chemiluminescence, comprising:
   a housing for enclosing the sample in a sample compartment so that the sample is inside the housing in the absence of a source of light from outside of the housing;
   a chassis within the housing comprising a conductive material;
   a first light sensor inside the housing for generating a sample signal in response to detecting the chemiluminescence;
   a second light sensor inside the housing shielded from the chemiluminescence and generating a reference signal;
   a controller inside the housing receiving the sample and reference signal to output a resulting signal indicative of the sample and determined as the difference between the sample and reference signals;
   a transparent window in the sample compartment, covered with an electro-conductive coating in electrical contact with the chassis, and having a filter which is a bandpass filter or a band-limited filter upstream from the first light sensor and a door spaced from the window; and
   an optic including a pair of plano-convex lens opposedly oriented between a consumable and the transparent window to focus and then spread the light, wherein in use the consumable comprising an entity on a swab for generating the chemiluminescence in the presence of the sample has been used to swab a surface to collect the sample to be tested, is inserted through the door into the sample compartment to bring the sample towards the transparent window, and wherein the transparent window is spaced from the bottom of the consumable.

29. A hand-held assay device for measuring the presence of a sample generating chemiluminescence, comprising:
   a housing for enclosing the sample in a sample compartment so that the sample is inside the housing in the absence of a source of light from outside of the housing;
   a first light sensor inside the housing for generating a sample signal in response to detecting the chemiluminescence;
   a second light sensor inside the housing shielded from the chemiluminescence and generating a reference signal;

a controller inside the housing receiving the sample and reference signal to output a resulting signal indicative of the sample and determined as the difference between the sample and reference signals;

a transparent window in the sample compartment upstream from the first light sensor and a door spaced from the window; and software executed on the controller for determining the presence of an opening in the door and for generating a warning signal in response to the detection of the light from the opening;

wherein an entity on a swab in a consumable for generating the chemiluminescence in the presence of the sample has been used to swab a surface to collect the sample to be tested and inserted through the door into the sample compartment to bring the sample towards the window.

30. A hand-held assay device for detecting the presence of a sample generating chemiluminescence, comprising:

a housing with a closeable door for enclosing a removeable consumable containing the sample in a sample compartment of the housing so that the sample and the consumable are inside the housing in absence of a source of light from outside of the housing when the door is closed;

a detection assembly inside the housing for detecting the chemiluminescence in the sample compartment from the consumable and generating a sample signal in response to its detection;

a transparent window inside the housing between the sample compartment and detection assembly, said transparent window being covered with a conductive transparent coating to minimize the direct injection of static charge from the consumable;

a light source in the sample compartment which when activated emits light which projects through the transparent window and strikes the detection assembly to generate a reference signal; and a controller inside the housing and software executed on the controller for comparing the reference signal to a reference value so as to prevent the device from operating further unless the reference signal is below a threshold suggesting that light from outside of the housing is absent, and when the light source is turned off for determining whether a resulting signal processed in response to the sample signal generated by the detection assembly is indicative of the presence of the sample.

31. The hand-held assay device defined in claim 30 further comprising a chassis inside the housing made of a conductive material and in contact with the coating to act as a Faraday cage.

32. The hand-held assay device defined in claim 30 wherein the transparent conductive coating on the window is indium tin-oxide, ITO.

33. The hand-held assay device defined in claim 30 wherein the detection assembly comprises:

a first photodiode generating a sample signal in response to chemiluminescence a second photodiode shielded from the chemiluminescence and generating a reference signal;

a sample and reference switched integrators, each connected in series with the respective one of the first and second photodiodes and outputting integrated values of the sample and reference signals received by the controller, the reference signal being generated in response to environmental changes selected from the group consisting of temperature, humidity and a combination thereof, and software executed on the controller for subtracting the integrated value of the sample signal from the integrated value of the sample signal to determine the resulting signal.

34. The hand-held assay device defined in claim 30, further comprising software executed on the controller for detecting the presence of the consumable in the sample compartment.

35. The hand-held assay device defined in claim 33 wherein each of the integrators is provided with a respective integration bypass capacitor and a solid state switch connected in parallel to one another to provide the integrated values of the sample signal and the reference signal, the hand-held device further comprising software executed on the controller for opening/closing the solid state switches before measuring the resulting signal to discharge accumulated static charges.

36. A hand-held assay device for detecting the presence of a sample generating chemiluminescence, comprising:

a housing provided with a sample compartment for enclosing the sample so as to generate the chemiluminescence in the sample compartment so that the sample is inside the housing in absence of a source of a light from outside of the housing;

a detection assembly inside the housing for detecting the chemiluminescence and generating a signal in response to its detection;

a transparent window inside the housing between a sample chamber and detection assembly, said transparent window being covered with a conductive transparent coating to minimize the direct injection of static charge and wherein the transparent window has opposite sides, one of which is coated with indium tin oxide, ITO, providing a shutterless structure of the hand-held device, whereas the other side of the transparent window has a bandpass filter selected from the group of a coating and a whole body; and a controller inside the housing for determining whether a resulting signal processed in response to the signal generated by the detection assembly is indicative of the presence of the sample.

37. A hand-held assay device for detecting the presence of a sample generating chemiluminescence, comprising:

a housing provided with a sample compartment for enclosing the sample so as to generate the chemiluminescence in the sample compartment so that the sample is inside the housing in absence of a source of a light from outside of the housing;

a detection assembly inside the housing for detecting the chemiluminescence and generating a signal in response to its detection;

a transparent window inside the housing between a sample chamber and detection assembly, said transparent window being covered with a conductive transparent coating to minimize the direct injection of static charge, wherein a first photodiode is juxtaposed with the side of the transparent window provided with a bandpass filter; and a controller inside the housing for determining whether a resulting signal processed in response to the signal generated by the detection assembly is indicative of the presence of the sample.

38. A hand-held assay device for detecting the presence of a sample generating chemiluminescence, comprising:
- a housing provided with a sample compartment for enclosing the sample so as to generate the chemiluminescence in the sample compartment so that the sample is inside the housing in absence of a source of a light from outside of the housing;
- a detection assembly inside the housing for detecting the chemiluminescence and generating a signal in response to its detection;
- a transparent window inside the housing between a sample chamber and detection assembly, said transparent window being covered with a conductive transparent coating to minimize the direct injection of static charge; and
- a controller inside the housing for determining whether a resulting signal processed in response to the signal generated by the detection assembly is indicative of the presence of the sample; and
- an LED mounted in the sample compartment to emit a beam of light projecting through the window and striking a first photodiode which generates a signal, and software executed on the controller for comparing the signal generated by the first photodiode to an LED reference value to provide a calibration value indicative of the cleanliness of the transparent window and accounted for during detection of the resulting signal.

39. A hand-held assay device for detecting the presence of a sample generating chemiluminescence, comprising:
- a housing provided with a sample compartment receiving the sample;
- a source of light mounted in the housing and emitting a beam of light extending along a path;
- a detection assembly along the path for generating a resulting signal in response to the chemiluminescence;
- a transparent window along the path between the sample compartment and the detection assembly, the detection assembly generating a calibration signal indicating cleanliness of the transparent window in response to being struck by the beam of light from the source; and
- a controller having an analytical mode, wherein the resulting signal is evaluated, and a calibration mode, wherein the calibration signal is evaluated.

40. The hand-held assay device defined in claim 39 wherein the detection assembly comprises:
- a first photodiode generating a sample signal in response to chemiluminescence;
- a second photodiode shielded from the chemiluminescence and generating a reference signal;
- a sample and reference switched integrators, each connected to the respective one of the first and second photodiodes and outputting integrated values of the sample and reference signals received by the controller, the reference signal being generated in response to environmental changes selected from the group consisting of temperature, humidity and a combination thereof,
- software executed on the controller in the analytical mode for subtracting the integrated value of the sample signal from the value of the sample signal to determine an integrating value of the resulting signal, and
- software executed on the controller for comparing the integrated value of the resulting signal to a sample threshold and for outputting the integrating value of the resulting signal if the value of the resulting signal is at least equal to the sample threshold.

41. The hand-held assay device defined in claim 39 wherein the, source of light is an LED pressed in a peripheral wall of the sample compartment, said controller being provided with software for comparing the measured calibration signal with a reference calibration signal and displaying an error signal if the measured calibration signal is not within the expected range of the reference calibration signal.

42. The hand-held device defined in claim 40, further comprising software executed on the controller for adjusting the resulting signal for the calibration signal if the latter is being within the expected range of the reference calibration signal.

43. The hand-held device defined in claim 42, further comprising software executed on the controller for comparing the resulting signal with a predetermined threshold and for outputting a signal indicative of the presence of the sample if the resulting signal is at least equal to the predetermined threshold.

44. The hand-held assay device defined in claim 42 wherein the detection assembly comprises:
- a first photodiode generating a sample signal in response to the chemiluminescence
- a second photodiode shielded from the chemiluminescence and generating a reference signal;
- sample and reference switched integrators, each connected to the respective one of the first and second photodiodes and outputting integrated values of the sample and reference signals received by the controller, the reference signal being generated in response to environmental changes selected from the group consisting of temperature, humidity and a combination thereof.

45. The hand-held assay device defined in claim 42, further comprising a source of light mounted in the sample compartment, and software executed on the controller for comparing a consumable-present signal with high, mid and low level values of an expected intensity of the light from the source of light.

46. The hand-held device defined in claim 44, further comprising software executed on the controller in a detection mode for turning a source of light on and software for determining a signal generated by the detection assembly in response to the turning the source of light off.

47. The hand-held device defined in claim 45, further comprising software executed on the controller for turning he source of light on and for determining a signal generated by the detection assembly in response to turning the source of light on, software executed on the controller for subtracting the determined signal with the source of light off from the determined signal of the source of light off to calculate the difference between the determined signals.

48. The hand-held device defined in claim 46, further comprising software executed on the controller for outputting a signal indicative of the absence of a consumable in the sample compartment if the difference between the determined signals is within a predetermined range having a low level and a high level, wherein the low level corresponds to the reference signal generated by the second photodiode, and the high level correspond to a signal representing the expected intensity of the source of light.

49. The hand-held device defined in claim 48 wherein the detection assembly comprises:
- a first photodiode generating a sample signal in response to the detection of the chemiluminescence;

a second photodiode shielded from the chemiluminescence and generating a reference signal;

sample and reference switched integrators, each connected to the respective one of the first and second photodiodes and outputting integrated values of the sample and reference signals received by the controller, the reference signal being generated in response to environmental changes selected from the group consisting of temperature, humidity and a combination thereof.

50. The hand-held device defined in claim 48, further comprising software executed on the controller in a first mode for subtracting the integrated value of the reference signal from the integrating value of the sample signal to determine a value of the first signal, and software executed on the controller for comparing the value of the first signal to a predetermined threshold to output a signal indicative of the presence of the sample if the value of the first signal is at least equal to the predetermined threshold.

51. The hand-held device defined in claim 48 further comprising software executed on the controller working in a second mode for turning the source of light, and software executed on the controller for comparing a second signal with a reference signal representing the expected intensity of the source of light, and software executed on the controller for displaying a warning signal if the second signal is beyond the expected intensity range of the source of light.

52. The hand-held device defined in claim 50 wherein the expected intensity range of the source of light having low and high levels, the hand-held device further comprising software executed on the controller for comparing a second signal with the high level to detect the presence of the consumable if the second signal exceeds the high intensity level at a predetermined value, and software for switching the controller from a the third mode to the first mode in response to the detection of the consumable.

53. The hand-held device defined in claim 50 the hand-held device further comprising software executed on the controller for switching the controller from a third mode to the first mode if a second signal is above the high intensity level at a predetermined value to indicate the presence of the consumable in the sample compartment.

54. The hand-held assay device defined in claim 48 wherein the transparent bottom having opposite sides, one of which is coated with indium tin oxide, ITO, to provide a shutterless structure of the hand-held device.

55. A hand-held assay device for detecting the presence of a sample generating chemiluminescence, comprising:

a housing provided with a sample compartment; with a closeable door for enclosing a consumable for collecting the sample and which is removably inserted into the sample compartment of the housing so that the sample and the consumable are inside the housing in the absence of a source of light from outside of the housing when the door is closed;

a detection assembly located in the housing along a path and juxtaposed with the consumable upon insertion of the consumable into the sample compartment, the detection assembly generating a resulting signal in response to the chemiluminescence and generating a consumable-present signal in response to detecting the consumable; and a controller preventing the device from operating further unless a source of light from outside of the housing is absent and having an analytical mode, wherein the resulting signal is evaluated, and a detection mode, wherein the consumable-present signal is evaluated.

56. A hand-held assay device for detecting the presence of a sample generating chemiluminescence, comprising:

a housing provided with a sample compartment;

a consumable adapted to be removably inserted in the sample compartment after collecting the sample, the sample compartment being provided with a transparent bottom;

a source of light provided in the sample compartment and emitting a beam of light which projects through the transparent bottom;

a detection assembly juxtaposed with the transparent bottom for generating a first signal in response to detection of the chemiluminescence and a second signal in response to being struck by the beam of light; and a controller receiving the first and second signals and having a first mode, wherein the first signal is evaluated to determine the presence of the sample, a second mode, wherein the second signal is evaluated to determine the cleanliness of the transparent bottom, and a third mode, wherein the second signal is determined to be indicative of the presence of the consumable.

57. A method of measuring the presence of a sample generating chemiluminescence, comprising the steps of:

providing a first photodiode for generating a sample signal in response to detecting the chemiluminescence, providing a second photodiode shielded from the chemiluminescence for generating a reference signal;

providing a closeable door allowing access to a sample compartment containing the sample in the absence of a source of light from outside of the sample compartment when the door is closed;

providing a controller receiving the sample signal and reference signal for preventing further operation in response to light from outside of the housing as determined by software executed on the controller which generates a warning signal in response to the detection of the light indicative of an open door, and subtracting the reference signal from the sample signal to determine a resulting signal; and comparing the resulting signal with a predetermined threshold signal; and displaying the resulting signal indicative of the sample if the resulting signal is at least equal to the threshold value.

58. The method defined in claim 57 further comprising the step of incrementally increasing the integration time if the resulting signal is less than the threshold, and of monitoring the integration time to prevent further detection of the sample and reference signals if the integration time has reached a predetermined limit.

59. The method defined in claim 57 further comprising the step of detecting a consumable containing the sample in the sample compartment, sample compartment being provided with a transparent bottom.

60. A method for detecting the presence of a sample generating chemiluminescence, comprising the steps of:

providing a housing having a sample compartment formed with a transparent bottom;

providing a closeable door allowing access to the sample compartment containing the sample in the absence of a source of light from outside of the sample compartment when the door is closed;

activating a source of light in the sample compartment;

generating a resulting signal from the source of light;

continuing detection if the resulting signal does not exceed a level expected of a test signal when there is an absence of a source of light from outside of the housing;

detecting the chemiluminescence and generating a signal in response to the detection;

providing a film of a conductive material on the transparent bottom, thereby minimizing the direct injection of static charge; and comparing the signal with a predetermined threshold; and displaying a value of the signal if the signal is at least equal to the predetermined threshold.

61. A method for detecting the presence of a sample generating chemiluminescence, said sample being placed in a sample compartment provided in a housing, comprising the steps of:

providing a closeable door allowing access to the sample compartment containing the sample in the absence of a source of light from outside of the sample compartment when the door is closed;

activating a source of light in the sample compartment;

generating a resulting signal from the source of light;

continuing detection if the resulting signal does not exceed a level expected of a test signal when there is an absence of a source of light from outside of the housing;

generating a sample signal in response to detecting the chemiluminescence;

generating a reference signal in response to detecting environmental changes selected from the group consisting of humidity, temperature drifts and a combination thereof;

integrating the sample and reference signals during a controllable integration period to produce integrated values of the sample and reference signals;

digitizing the integrated values of the sample and reference signals;

subtracting the digitized value of the reference signal from the digitized value of the sample signal to determine a value of a resulting signal;

comparing the value of the resulting signal with a predetermined threshold and displaying the resulting signal indicative of the presence of the sample if the value of the resulting signal is at least equal to the threshold.

62. A method for detecting the presence of a sample generating chemiluminescence, said sample being placed in a sample compartment provided in a housing, comprising the steps of:

generating a sample signal in response to detecting the chemiluminescence;

generating a reference signal in response to detecting environmental changes selected from the group consisting of humidity, temperature drifts and a combination thereof;

integrating the sample and reference signals during a controllable integration period to produce integrated values of the sample and reference signals;

digitizing the integrated values of the sample and reference signals;

subtracting the digitized value of the reference signal from the digitized value of the sample signal to determine a value of a resulting signal; comparing the value of the resulting signal with a predetermined threshold and displaying the resulting signal indicative of the presence of the sample if the value of the resulting signal is at least equal to the threshold; and determining the cleanliness of the transparent bottom before determining the resulting signal.

* * * * *

UNITED STATES PATENT AND TRADEMARK OFFICE
CERTIFICATE OF CORRECTION

PATENT NO. : 6,927,851 B2
DATED : August 9, 2005
INVENTOR(S) : John T. McCaffrey, Szilveszter Jando and Sunita Carrasko It is certified that error appears in the above-identified patent and that said Letters Patent is hereby corrected as shown below:

Title page,
Item [57], ABSTRACT,
Line 2, "by as ample of" should be -- by a sample of --.

Column 3,
Line 7, "many photodecting transducers" should be -- many photodetecting transducers --.

Column 4,
Line 14, "determine integration" should be -- determined integration --.
Line 38, "effect these change have" should be -- effect these changes have --.
Line 63, "in accordance one embodiment" should be -- in accordance with one embodiment --.

Column 9,
Line 49, "made of glass has its side" should be -- made of glass as its side --.
Line 64, "or is a made of" should be -- or is made of --.

Column 18,
Line 49, "he source of light" should be -- the source of light --.

Column 19,
Line 35, "from a the third mode" should be -- from the third mode --.

Signed and Sealed this

Twenty-fifth Day of October, 2005

JON W. DUDAS
*Director of the United States Patent and Trademark Office*